(12) United States Patent
Lacombe et al.

(10) Patent No.: US 8,267,869 B2
(45) Date of Patent: Sep. 18, 2012

(54) MULTI-PURPOSE BIOPSY FORCEPS

(75) Inventors: Francois Lacombe, Chaville (FR); David Hughett, Liberty Township, OH (US); Chris Tihansky, Doylestown, PA (US); Magalie Genet, Guyancourt (FR)

(73) Assignee: Manua Kea Technologies, Paris (FR)

( * ) Notice: Subject to any disclaimer, the term of this patent is extended or adjusted under 35 U.S.C. 154(b) by 175 days.

(21) Appl. No.: 12/651,238

(22) Filed: Dec. 31, 2009

(65) Prior Publication Data

US 2010/0168610 A1 Jul. 1, 2010

Related U.S. Application Data

(60) Provisional application No. 61/141,995, filed on Dec. 31, 2008.

(51) Int. Cl.
*A61B 10/04* (2006.01)
(52) U.S. Cl. .................................................... 600/564
(58) Field of Classification Search ............... 600/564, 600/562
See application file for complete search history.

(56) References Cited

U.S. PATENT DOCUMENTS

| | | | | |
|---|---|---|---|---|
| 5,782,397 A * | 7/1998 | Koukline | ................... | 227/176.1 |
| 5,807,261 A * | 9/1998 | Benaron et al. | ............... | 600/473 |
| 6,071,233 A * | 6/2000 | Ishikawa et al. | ............... | 600/104 |
| 6,129,683 A * | 10/2000 | Sutton et al. | ................... | 600/564 |
| 6,139,508 A * | 10/2000 | Simpson et al. | ............... | 600/564 |
| 6,155,988 A * | 12/2000 | Peters | ........................... | 600/564 |
| 6,926,676 B2 * | 8/2005 | Turturro et al. | ............... | 600/562 |
| 7,297,121 B2 * | 11/2007 | Turturro et al. | ............... | 600/563 |
| 7,833,167 B2 * | 11/2010 | Kortenbach et al. | .......... | 600/564 |
| 2004/0181169 A1 * | 9/2004 | Diamond et al. | ............. | 600/564 |
| 2004/0215132 A1 * | 10/2004 | Yoon | ............................... | 604/57 |
| 2005/0245841 A1 * | 11/2005 | Turturro et al. | ............... | 600/562 |
| 2005/0288546 A1 * | 12/2005 | Sonnenschein et al. | ...... | 600/101 |
| 2006/0069304 A1 * | 3/2006 | Takemoto et al. | ............ | 600/104 |
| 2006/0084885 A1 * | 4/2006 | Reydel | .......................... | 600/564 |
| 2006/0106283 A1 * | 5/2006 | Wallace et al. | ............... | 600/109 |
| 2006/0271066 A1 * | 11/2006 | Kimura et al. | ................ | 606/108 |
| 2007/0077045 A1 * | 4/2007 | Kato | ............................... | 396/17 |
| 2007/0135686 A1 * | 6/2007 | Pruitt et al. | ................... | 600/214 |
| 2007/0293720 A1 * | 12/2007 | Bayer | .......................... | 600/112 |
| 2008/0058590 A1 * | 3/2008 | Saadat et al. | .................. | 600/109 |
| 2008/0281299 A1 * | 11/2008 | Menn | ............................... | 606/1 |
| 2009/0171160 A1 * | 7/2009 | Ito et al. | ........................ | 600/141 |
| 2009/0287114 A1 * | 11/2009 | Lee et al. | ...................... | 600/566 |
| 2010/0168610 A1 * | 7/2010 | Lacombe et al. | ............. | 600/564 |
| 2010/0228221 A1 * | 9/2010 | Kassab et al. | ................. | 604/500 |
| 2011/0060188 A1 * | 3/2011 | Sharon et al. | ................. | 600/106 |
| 2011/0112551 A1 * | 5/2011 | Adams et al. | ................. | 606/142 |

* cited by examiner

*Primary Examiner* — Max Hindenburg
*Assistant Examiner* — Michael C Stout
(74) *Attorney, Agent, or Firm* — Osha Liang LLP

(57) ABSTRACT

A method to perform an endoscopic biopsy includes deploying a mechanical forceps through an accessory channel of an endoscope assembly, deploying an optical probe through the accessory channel to an area of investigation, optically evaluating tissue at the area of investigation, actuating the mechanical forceps to grasp a sample of the tissue, and retrieving the mechanical forceps and the optical probe through the accessory channel of the endoscope assembly. A biopsy apparatus includes a delivery conduit, an optical probe configured to investigate the tissue upon a distal end of an optical conduit extending through the delivery conduit, and a forceps assembly slidably engaged over the optical conduit, the forceps assembly comprising jaws configured to operate between a closed position and at least one open position, wherein the jaws of the forceps are urged into the closed position as the forceps are retracted within the delivery conduit.

18 Claims, 17 Drawing Sheets

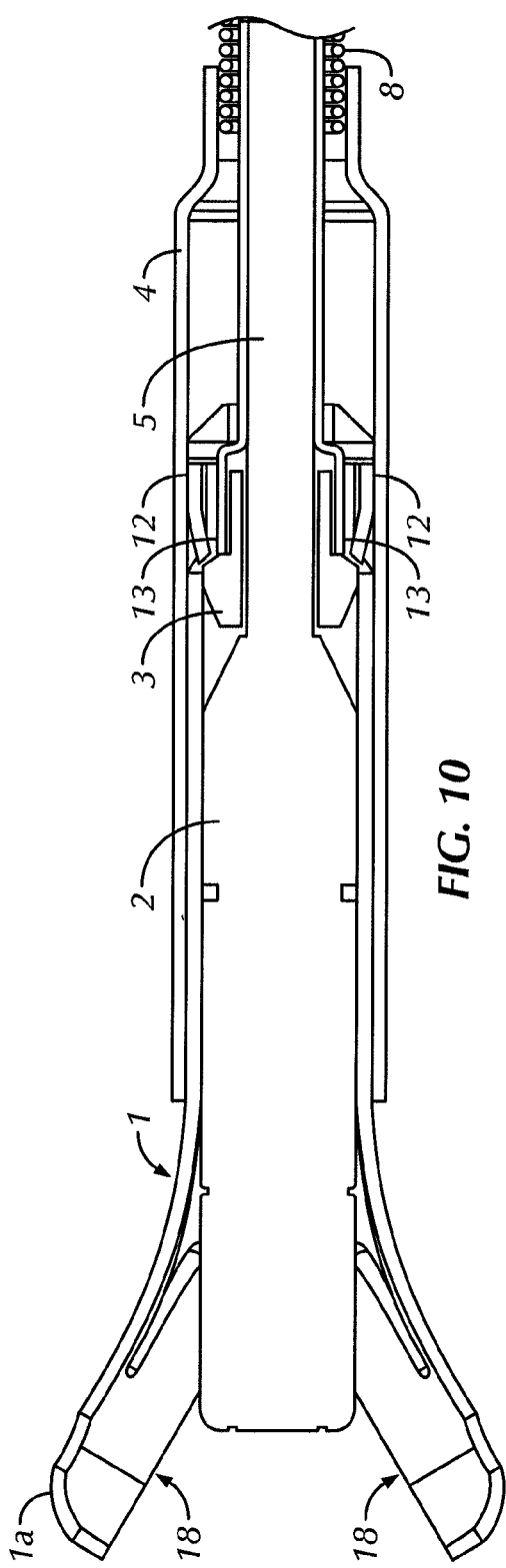
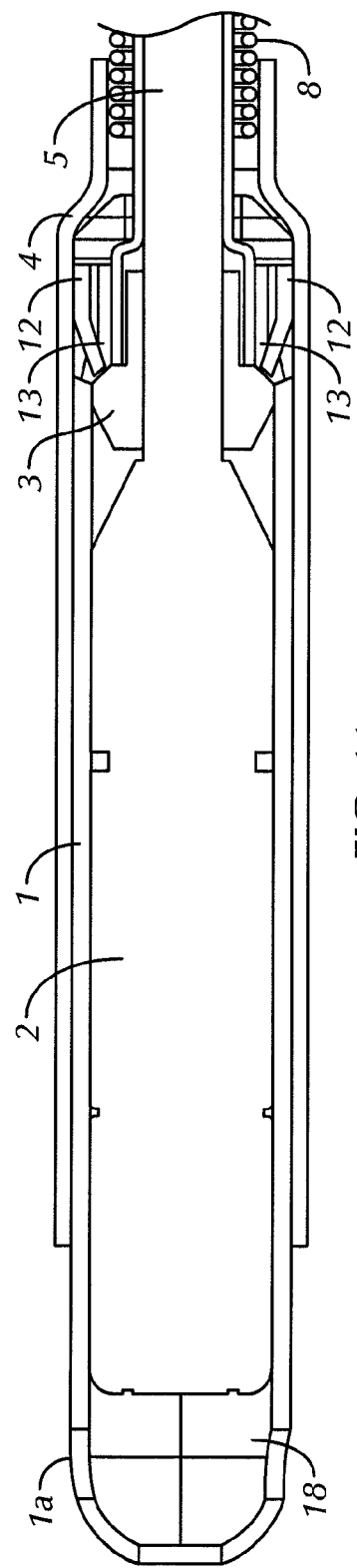

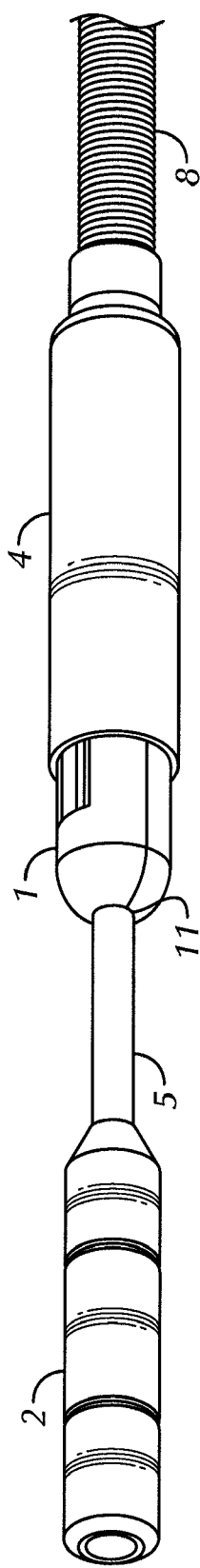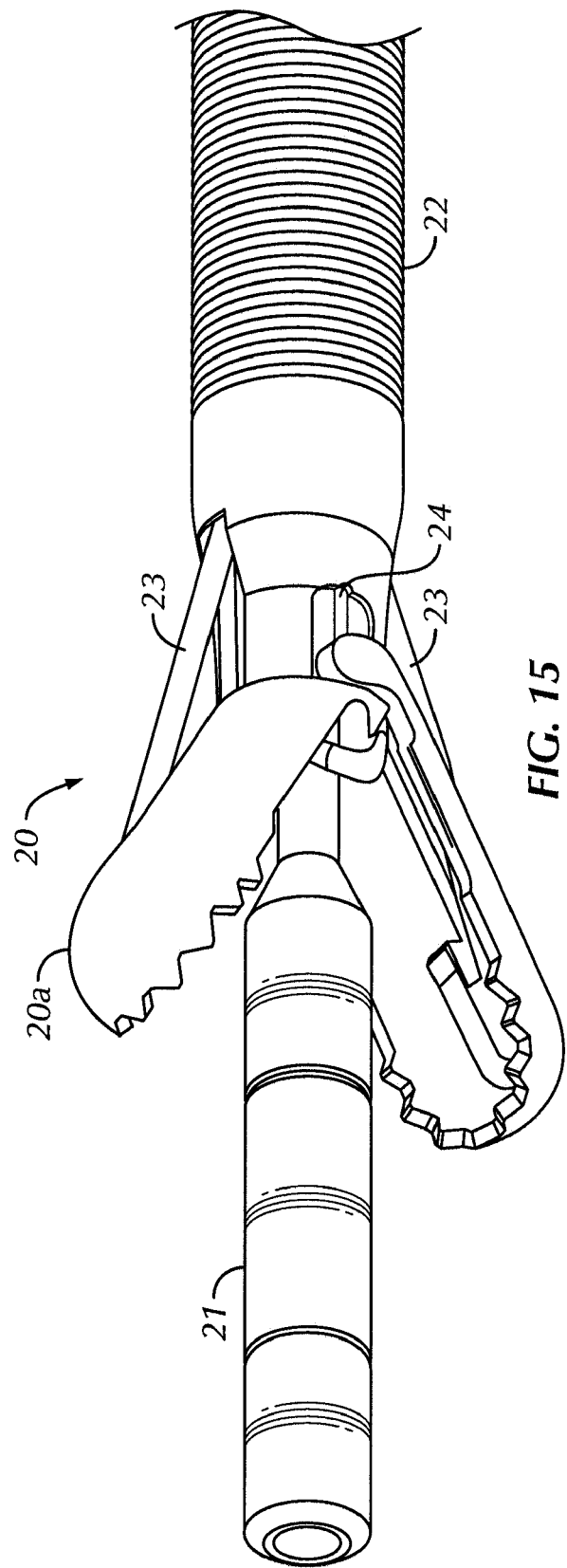

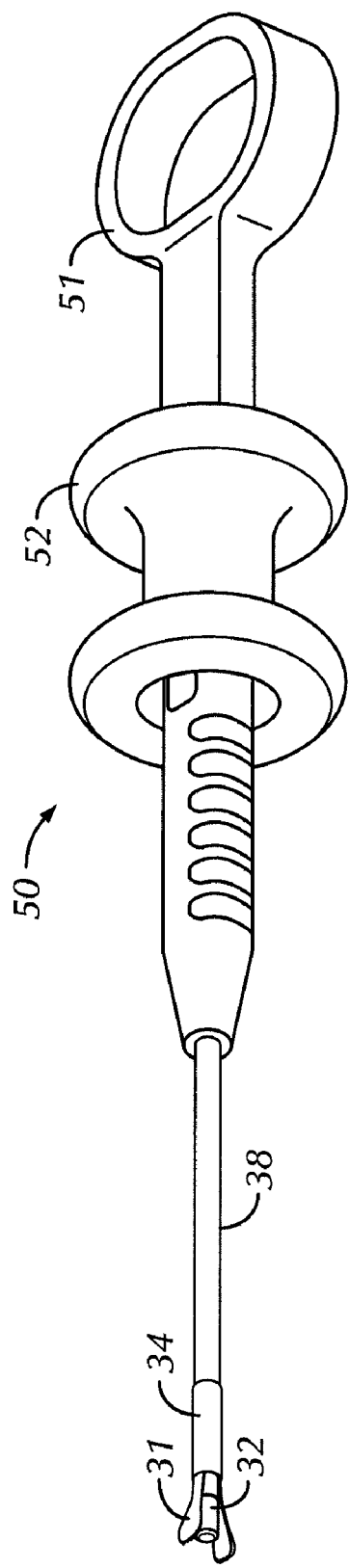
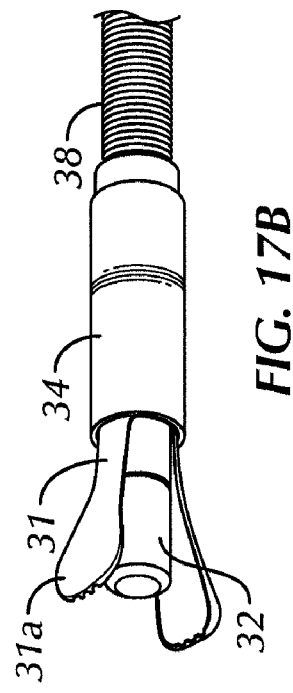
FIG. 17A
FIG. 17B

MULTI-PURPOSE BIOPSY FORCEPS

CROSS-REFERENCE TO RELATED APPLICATIONS

The present application claims priority to U.S. Provisional Patent Application Ser. No. 61/141,995, filed on Dec. 31, 2008, hereby incorporated by reference in its entirety.

BACKGROUND OF THE DISCLOSURE

1. Field of the Disclosure

The present disclosure relates to biopsy forceps compatible with endoscopic tools. More particularly, the present disclosure relates to biopsy forceps compatible with optical biopsy tools such that samples of the as-optically biopsied tissue may be retrieved for further analysis.

2. Description of the Related Art

A biopsy is a medical test involving the removal of cells or tissues for examination, referred to throughout as a mechanical biopsy. After extraction from a patient, the tissue is generally examined under a microscope by a pathologist, and may also be analyzed chemically. When an entire lump or suspicious area is removed, the procedure is called an excisional biopsy. When only a portion of tissue (e.g., a sample) is removed with preservation of the histological architecture of the tissue's cells, the procedure may be called an incisional biopsy or a core biopsy. When a sample of tissue or fluid is removed with a needle in such a way that cells are removed without preserving the histological architecture of the tissue cells, the procedure may be called a needle aspiration biopsy. Biopsies are generally performed for diagnosis and early detection of pathologies and are often used for follow-up of pathologies.

In the particular case of rigid or flexible endoscopy, either in pulmonology or in gastroenterology, incisional biopsies are typically performed with a forceps. A typical forceps 100 (e.g., as shown in FIG. 1) comprises an incisional device 101, (e.g., a pair of miniaturized jaws) which may be inserted into the patient's body to a region of interest through an accessory channel of an endoscope (not shown). The forceps may be actuated from outside of the patient's body by operation of handle 102. The biopsy may be performed by the endoscopist or his assistant under video control and observation from the endoscope. After the forceps is closed, and a sample is extracted from the tissue of interest, it may be retracted from the endoscope so that the sample may be retrieved and analyzed by a pathologist. Each time the forceps is used, a volume of tissue up to about a few cubic millimeters may be removed and the same forceps may be re-used during the same procedure. Conventionally, forceps may be used successively in an organ or in a single patient, but they may not be used in different patients (or, in certain instances, in different organs) to prevent cross-contamination. Therefore, forceps have historically been sold as disposable items.

For mechanical biopsies, an alternative to jaws 101 may be snares, as shown in FIG. 2. Biopsy snares permit grabbing structures with a sufficient vertical extension over the surface of the mucosa. Snares may be preferred for certain tangential biopsies, for example, polypectomies.

Additionally, an alternative to mechanical biopsies has recently developed. The new procedure consists of inserting an optical device (as opposed to a mechanical device) into the accessory channel of the endoscope 110 (e.g., as shown in FIG. 3) that is specifically designed to perform an optical analysis of the internal layers of the mucosa. For example, a fiber optic "microscope" (optical biopsy probe) 111 may be delivered to tissue from within an accessory channel of an endoscope to micro-analyze the area of investigation in-situ. Because these techniques, also called optical biopsies, are not invasive, they may be repeated ad libitum, and a much larger portion of the mucosa may be searched for areas of interest.

Even in view of the advantages of optical biopsies, mechanical biopsies may be preferred. The preference may result from the highly detailed analysis of an obtained sample that may be performed by the pathologist and because a much larger amount of histological data may exist. Therefore, the mechanical biopsy procedure is considered as a reference, or gold standard. However, a drawback to the "gold standard" is that at very early stages of a pathology the biopsy procedure may be conducted randomly or blindly. Such a practice may unfortunately lead to a large number of false negatives (i.e., situations were a pre-malignant or malignant condition is not detected).

In this context, optical biopsies may be envisioned as a preliminary and complementary procedure that may be used for identifications for subsequent mechanical biopsies. The combination of both techniques may not only reduce the number of false negatives (and consequently increase the overall accuracy of the biopsy process), but also may reduce the overall cost of diagnostic procedures.

A typical pair of biopsy forceps 100 is shown in FIG. 1. The forceps 100 comprise a pair of jaws 101 mounted at a distal end of a sheath 104 and a handle 102 is disposed at the proximal end of the sheath. Handle 102 may be connected to a wire 105 (see FIG. 6) that, through sheath 104, controls the opening or the closing of jaws 101. Jaws 101 may be a few millimeters in length and the sheath 104 may be, as is typical, a metallic coil that may be 2 to 3 meters long.

Various mechanisms exist to operate the jaws of the forceps with appropriate movements and amplitude and with a desirable amount of strength. Biopsy forceps currently available may be divided into one of two categories, levers or pantographs (e.g., FIG. 4) and pivots (e.g., FIG. 5). Both solutions work on the principle of two opposite and combined actions. Referring to FIG. 6, when an inner wire 105 pulls on the extremity of the pantograph or the pivot, while the outer sheath 104 pushes on the central articulation of the pantograph or on the jaws themselves, the jaws are closed.

Biopsy forceps may be equipped with different kinds of jaws (FIGS. 7A-7D) to facilitate grabbing different volumes of tissue, in different orientations, tangent or perpendicular, to the surface. Some jaws may also include a stinger 107 (FIG. 7C) to help immobilize the sample while closing the jaws. Currently, biopsy forceps may be provided by various suppliers, including, but not limited to: ABS; ASEPT INMED; MEDIGLOBE; BOSTON SCIENTIFIC; CONMED; COOK; EUROBIOPSY; LIFE EUROP PARTNERS; NET; and OLYMPUS.

As described above, optical biopsy probes are a new class of medical devices. Instead of extracting a sample from an area of interest, endoscopists may use optical biopsy probes to collect and analyze the light reflected or re-emitted by the tissue. One example of the light process is through fluorescence processes. Further, spectroscopy and imaging analysis techniques are commonly used through optical biopsy probes.

Spectroscopic optical biopsies include illuminating the tissue with a certain excitation radiation, generally in the UV range, and collecting the light with the optical biopsy probe that may be selectively remitted by the tissue. A spectroscopic analysis of this secondary radiation may then be performed. Because different molecules absorb and re-emit light differently, biological changes occurring at the cellular level during the development of a pathology may be detected and used to characterize this development. Optical fibers may transport excitation to the subject tissue and may also serve as a means of light collection. Both functions may be performed by a unique fiber, or by different fibers associated together in a fiber bundle. Excitation sources, dispersing elements, and detectors may be located outside the patient while light may travel inside the patient within the optical fibers.

Microscopic optical biopsies may include collecting the light coming from the area of investigation and forming an image instead of a spectrum. In this case, the pathology characterization may rely on the observation and identification of the microscopic changes of the tissue architecture. Images may be produced from the light scattered by microscopic heterogeneities in the tissue (reflectance microscopy) or from the light re-emitted by some fluorescence mechanism (fluorescence microscopy). In the latter case, the fluorescence may either be endogenous, as fluorescent molecules naturally exist in the tissue, or may be exogenous, because some fluorescent markers may have been delivered to the tissue.

To produce such an image, optical biopsy probes may consist of a fiber bundle equipped with distal optics to examine the tissue at different optical resolutions, fields of view, or working depths. The illumination light may either be sent through the entire bundle, or through individual fibers, sequentially. The former configuration may be regarded as a fibered version of an epi-illumination microscope. The latter configuration may be associated with a proximal scanning device which addresses each fiber successively. The complete system may therefore act as a fibered confocal microscope. Such an epi-illumination fiber based endomicroscope is marketed by Remincalm LLC. Mauna Kea Technologies markets a confocal fiber based endomicroscope, Cellvizio®.

Another process may involve a unique fiber that may be used to provide light illumination and collection. In this particular case, a miniaturized scanning mechanism may be mounted at the distal end of the fiber. Such fiber-based endomicroscope based on a microscopic distal scanner is available from Optiscan.

A fiber bundle and a distal scanner may be combined into a single unit. In these particular cases, one fiber may be used for the illumination while the rest of the bundle may collect the fluorescent light. Eric Seibel, from the HIT Lab, at University of Washington, has developed such a concept.

A large variety of endoscopic tools exist, including snares, knives, and needles. Furthermore, attempts have been made to implement a solution combining optical biopsy capability and a forceps capability. In such combinations, the fiber optics became part of the forceps mechanism. For instance, the wire, connected to the handle, which pulls on the lever or the pivot was replaced by the fiber itself. However, these solutions have been developed only for spectroscopy, and not in a configuration where distal optics were used.

SUMMARY OF THE CLAIMED SUBJECT MATTER

In one aspect, the present disclosure relates to a method to perform an endoscopic biopsy, the method comprising, deploying a mechanical forceps through an accessory channel of an endoscope assembly, deploying an optical probe through the accessory channel of the endoscope assembly to an area of investigation, optically evaluating tissue at the area of investigation, actuating the mechanical forceps to grasp a sample of the tissue, and retrieving the mechanical forceps and the optical probe from the area of investigation through the accessory channel of the endoscope assembly.

In another aspect, the present disclosure relates to a biopsy apparatus to investigate tissue through an accessory channel of an endoscope assembly including an optical probe configured to investigate the tissue upon a distal end of an optical probe body extending through the accessory channel and a forceps assembly slidably engaged over the optical probe body, the forceps assembly comprising jaws configured to operate between a closed position and at least one open position and wherein the jaws of the forceps are urged into the closed position as the forceps are retracted within the accessory channel.

In another aspect, the present disclosure related to a method to perform an optical biopsy with a biopsy apparatus, comprising deploying an optical probe and a forceps assembly to the area of investigation through the accessory channel, wherein the forceps are positioned behind the optical probe and jaws of the forceps assembly are closed about the optical probe body, performing an optical biopsy at the area of investigation with the optical probe, opening the jaws, retracting the optical probe within a probe volume of the forceps assembly, closing the jaws around a tissue sample, and retracting the forceps assembly and optical probe through the accessory channel.

In another aspect, the present disclosure relates to a biopsy forceps to investigate tissue through an accessory channel of an endoscope assembly, the biopsy forceps including a probe conduit extending through the biopsy forceps, wherein the probe conduit is configured to removably receive an optical probe on a distal end of an optical probe body, and a set of jaws configured to operate between a closed position and at least one open position.

In another aspect, the present disclosure related to a method to perform an optical biopsy using a biopsy forceps, comprising, deploying the biopsy forceps to an area of investigation through an accessory channel of an endoscope assembly, opening the biopsy forceps, deploying an optical probe on the distal end of an optical probe body to the area of investigation through a probe conduit of the open biopsy forceps, performing an optical biopsy at the area of investigation with the optical probe, retracting the optical probe at least partially through the probe conduit, closing the biopsy forceps around tissue at the area of investigation to be sampled, and retracting the biopsy forceps and the optical probe from the area of investigation through the accessory channel.

BRIEF DESCRIPTION OF DRAWINGS

Features of the present disclosure will become more apparent from the following description in conjunction with the accompanying drawings.

FIG. 10 is a cross-section of the disposable forceps in accordance with embodiments of the present disclosure.

FIG. 11 is a cross-section of the disposable forceps of FIG. 10 with the jaws of the forceps closed.

FIG. 14 is a view of disposable forceps in accordance with embodiments of the present disclosure.

FIG. 15 is a schematic view of an alternative optical biopsy forceps assembly in accordance with embodiments of the present disclosure.

FIG. 17A shows a biopsy unit in accordance with embodiments of the present disclosure. FIG. 17B is a close-view of the distal end of the biopsy unit of FIG. 17A.

DETAILED DESCRIPTION

The present disclosure includes new mechanical configurations where forceps may not be permanently attached to an optical device. Exemplary embodiments are discussed as follows, with reference to the Figures.

A first exemplary embodiment of the present disclosure is shown in FIGS. 8-14. In this first embodiment a biopsy unit may comprise a removable forceps and an optical probe. The forceps may comprise a pair of jaws that may be clipped onto an optical probe immediately before insertion into an accessory channel of an endoscope. The probe may be equipped with a mechanism to open and close the jaws through manipulation of a handle. After use, the jaws may be unclipped and separated from the optical probe. The jaws may then either be thrown away or disinfected separately (i.e., in a different or more rigorous process or machine).

Figure 8:
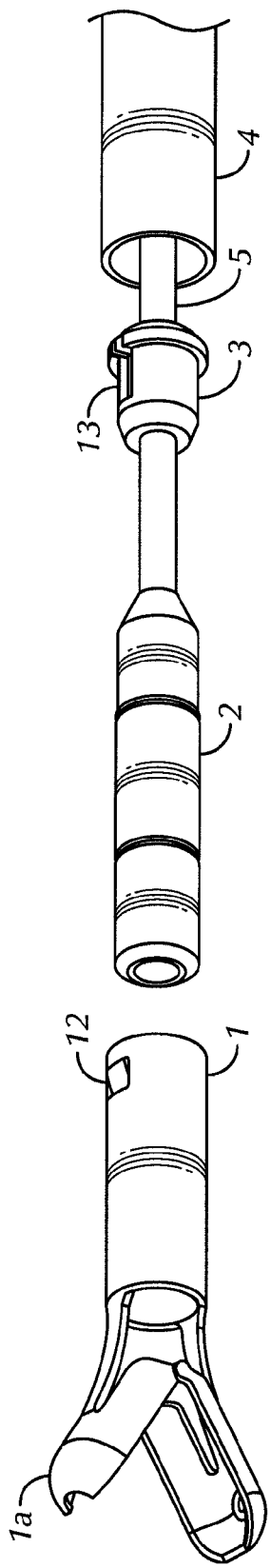
FIG. 8 is an exploded view of a disposable forceps in accordance with embodiments of the present disclosure.

Referring to FIG. 8, the forceps assembly 1 may be constructed from a single tubular structure. The proximal end of this structure may be left intact while the distal end may be split along its length into two halves which form jaws 1a. The intermediate portion, between the intact portion and the split portion, may be hollowed so that it may be relatively flexible and may be maneuvered to open or close jaws 1a.

Forceps assembly 1 may be made large enough to slide over the head of optical probe 2 and reach a ring 3 mounted on the optical probe body 5. The forceps assembly 1 may then be clipped to ring 3 to secure the forceps assembly 1 to the optical probe body 5. Forceps assembly 1 may be clipped, for example, by use of a tab-slot configuration, as shown in FIGS. 8-11. Tab 12 may be disposed on the proximal end of forceps assembly 1, and slot 13 may be disposed on ring 3.

Figure 9:
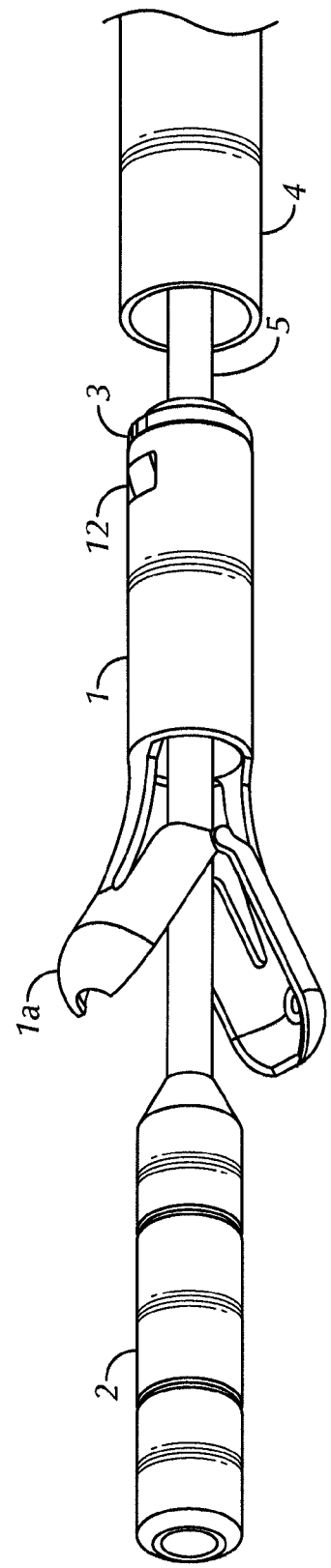
FIG. 9 is a view of the disposable forceps of FIG. 8 after the forceps are attached to the optical probe.
Figure 12:
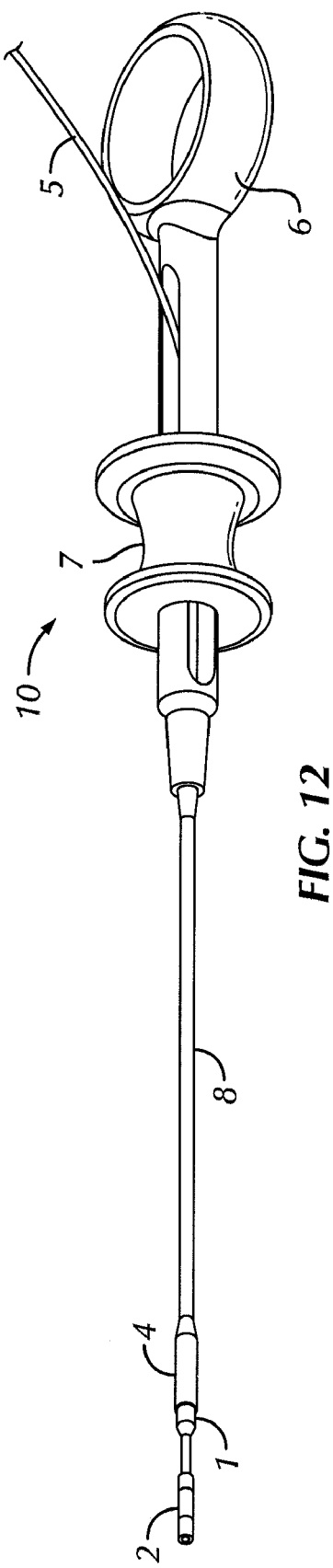
FIG. 12 is an assembly view drawing of disposable forceps in accordance with embodiments of the present disclosure.

Referring specifically to FIGS. 9 and 10, when clipped onto ring 3, forceps assembly 1 and ring 3 may slide together along the optical probe body 5. A sleeve 4 may mounted on the distal end of sheath 8. With a larger diameter than forceps assembly 1, sleeve 4 may cover forceps assembly 1, as shown in FIG. 10, and may allow closure of jaws 1a.

Figure 1:
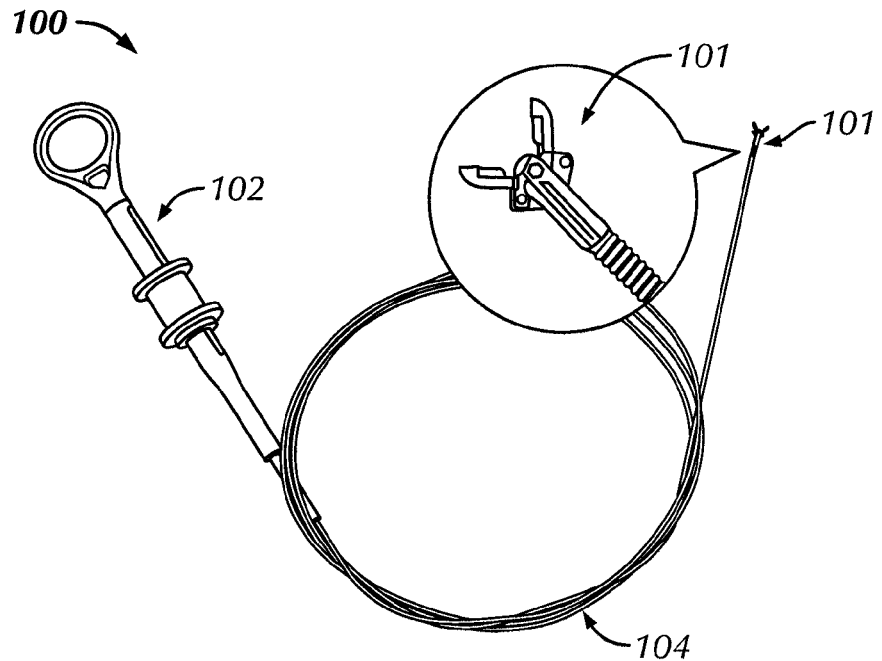
FIG. 1 is an exemplary representation of a set of biopsy forceps.
Figure 2:
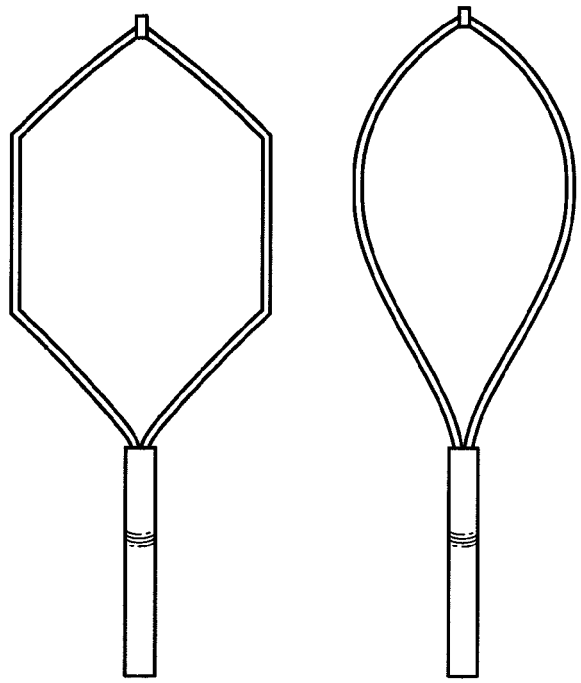
FIG. 2 is an exemplary representation of biopsy snares.
Figure 3:
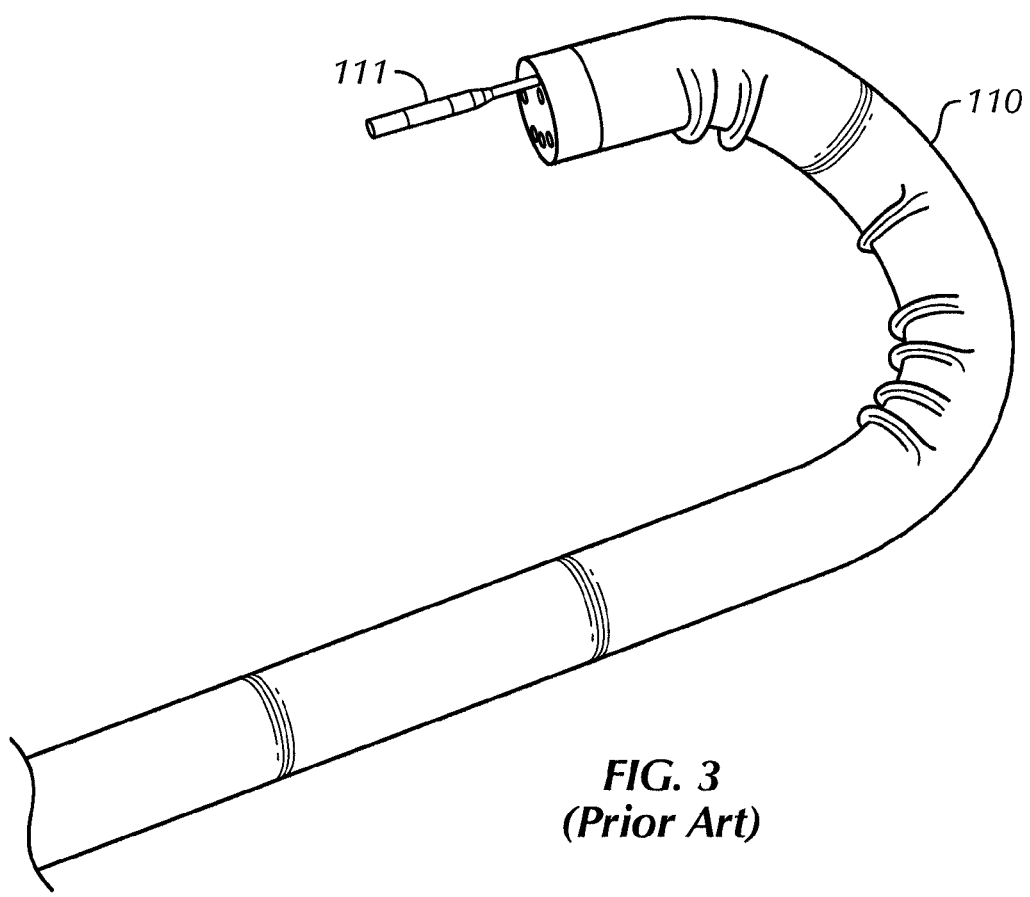
FIG. 3 is an example of an optical biopsy device exiting from an accessory channel of an endoscope.
Figure 4:
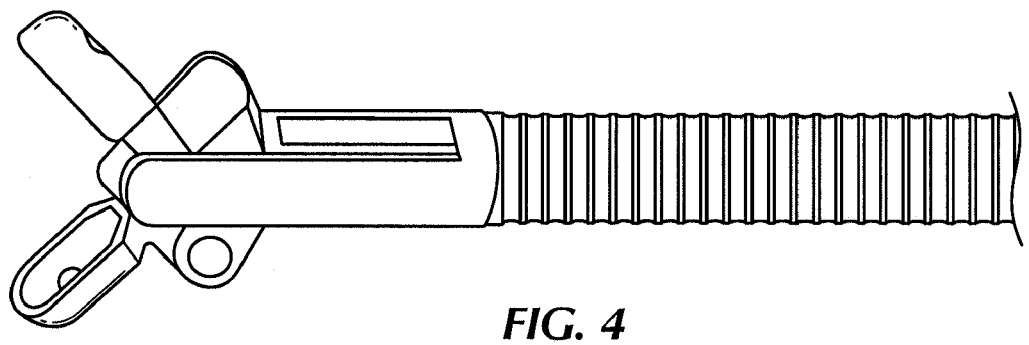
FIG. 4 is an example of a pantograph biopsy forceps.
Figure 5:
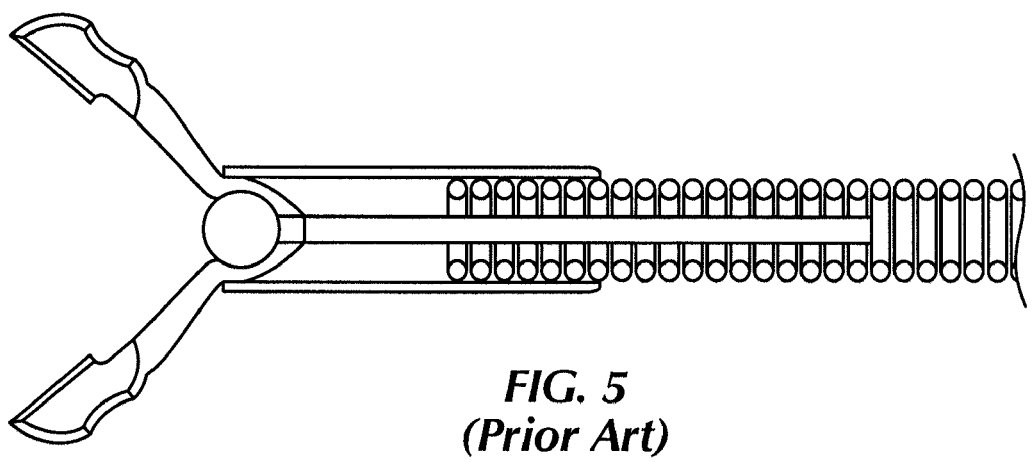
FIG. 5 is an example of a pivot biopsy forceps.
Figure 6:
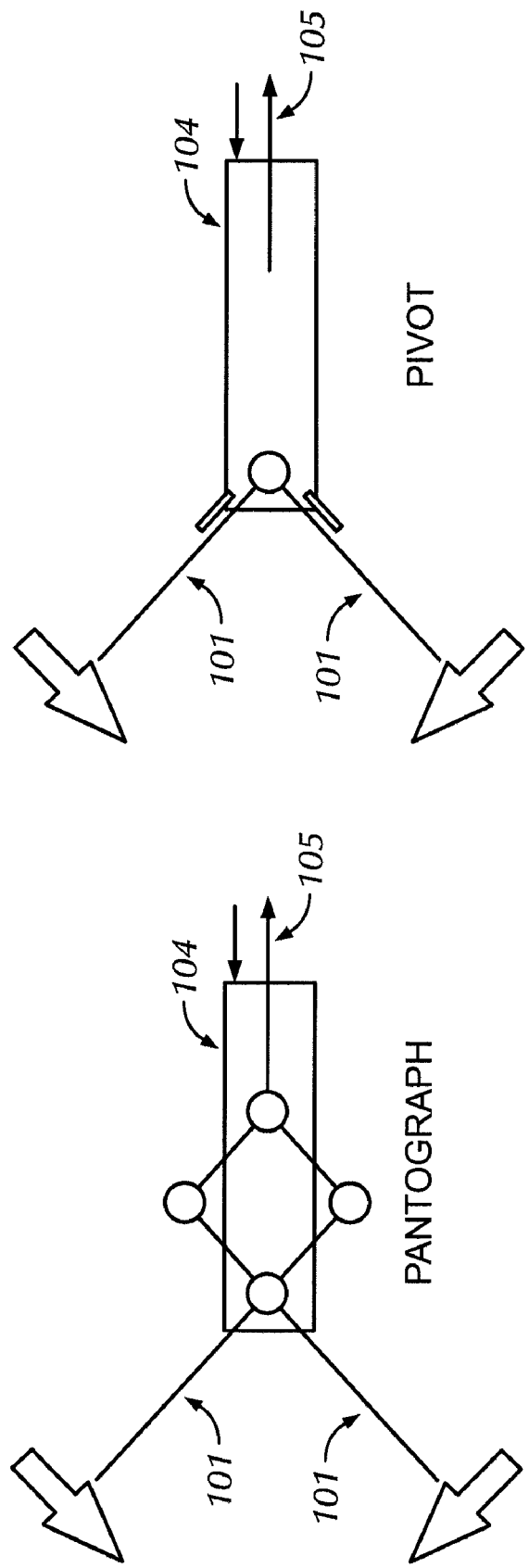
FIG. 6 is a schematic representation of the operation of pantograph and pivot style biopsy forceps.
Figure 7A:
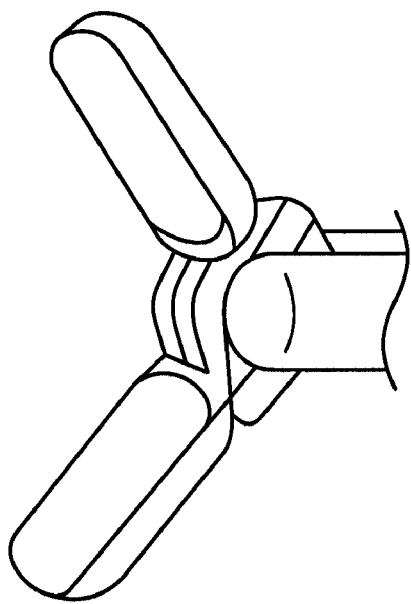
FIGS. 7A-7D are examples of: (A) simple biopsy forceps jaws; (B) windowed biopsy forceps jaws; (C) windowed and stingered biopsy forceps jaws; and (D) toothed biopsy forceps jaws.
Figure 7B:
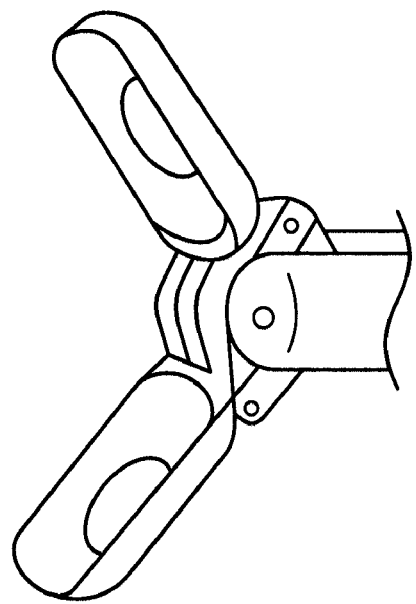
Figure 7C:
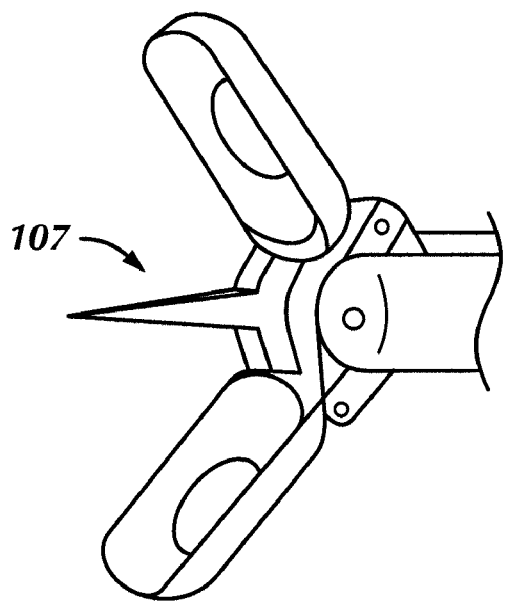
Figure 7D:
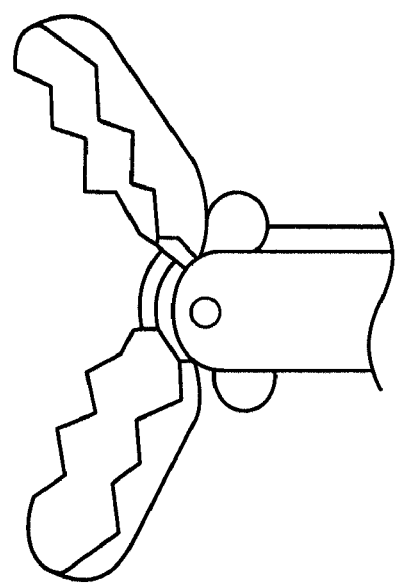

As sleeve 4 may be maneuvered toward the distal end of the biopsy unit, or forceps assembly may be maneuvered toward the proximal end of the biopsy unit (see FIG. 11), sleeve 4 may force jaws 1a to close and grab a volume of tissue that may be located just in front of the head of optical probe 2. In this respect, the movement may be similar to that of a pivot system depicted in FIGS. 5 and 6. The tissue may be captured in a sample volume 18, defined by the area within forceps assembly 1 behind jaws 1a and just in front of the lens of optical probe 2.

As shown, the forceps assembly 1 may be capable of at least two different movements: gliding along optical probe 2 and opening/closing. Both movements may be controlled by handle 10, located at the proximal end of the biopsy unit (see FIG. 12). Handle 10 may be made of two distinct parts: a main part 6, to be held with the thumb, and a sliding part 7, to be held, for example, between the forefinger and the middle finger.

Figure 13:
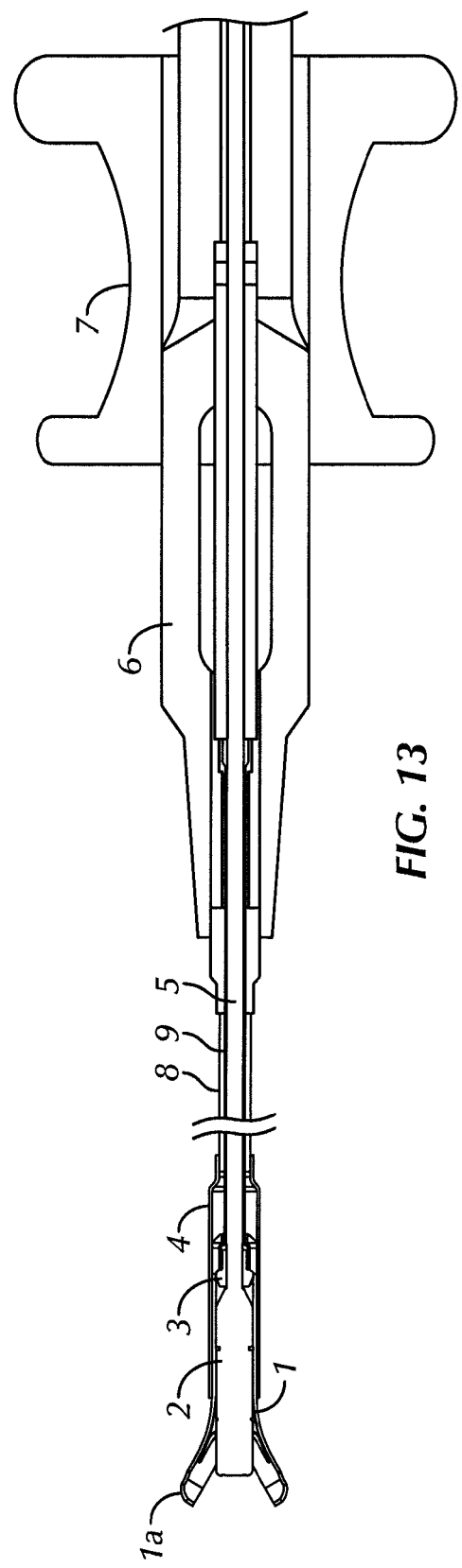
FIG. 13 is a cross-section of the assembly of FIG. 12.

Referring to FIG. 13, the main part 6 and the sleeve 4 may be linked together by a sheath 8. Sheath 8 may be made, for example, of a metallic coil, to provide flexibility and strength. Sliding part 7 and ring 3 (on which the forceps assembly 1 may be clipped) may be linked together with two wires 9 running along the optical probe body 5, inside sheath 8. A bulk movement of the handle 10 (with sliding part 7) may make the forceps assembly 1 slide along the optical probe body 5, while a relative movement of main part 6 with respect to sliding part 7, may make jaws 1a open or close.

According to this first exemplary embodiment, during an endoscopic procedure and before the optical examination, a forceps assembly 1 may first be clipped onto an optical probe 2, through attachment to ring 3. Forceps assembly 1 may then be disposed behind optical probe 2 and closed over the optical probe body 5, as shown in FIG. 14. A small aperture 11 may be formed in the distal end of jaws 1a and may allow for operation of jaws 1a without cutting or damaging the optical probe body 5.

The biopsy unit may then be inserted into the accessory channel of the endoscope to reach the area to the biopsied. Jaws 1a may then be opened so that the forceps assembly 1 may be pushed over the optical probe 2. With the forceps open, the endoscopist may scan the area by performing optical biopsies until a suspicious zone deserving a mechanical biopsy may be detected. Handle 10 may then be operated to close jaws 1a at the point of interest. Both the forceps assembly 1 and the optical probe 2 may then be retracted from the patient. The sample may be released, and both instruments may be used for another series of optical and mechanical biopsies within the same patient. When the procedure is completed, the endoscopist may dispose of the forceps assembly 1 and send the optical probe 2 to the disinfection unit. Alternatively, the forceps assembly 1 may be sent separately for disinfection.

Figure 16:
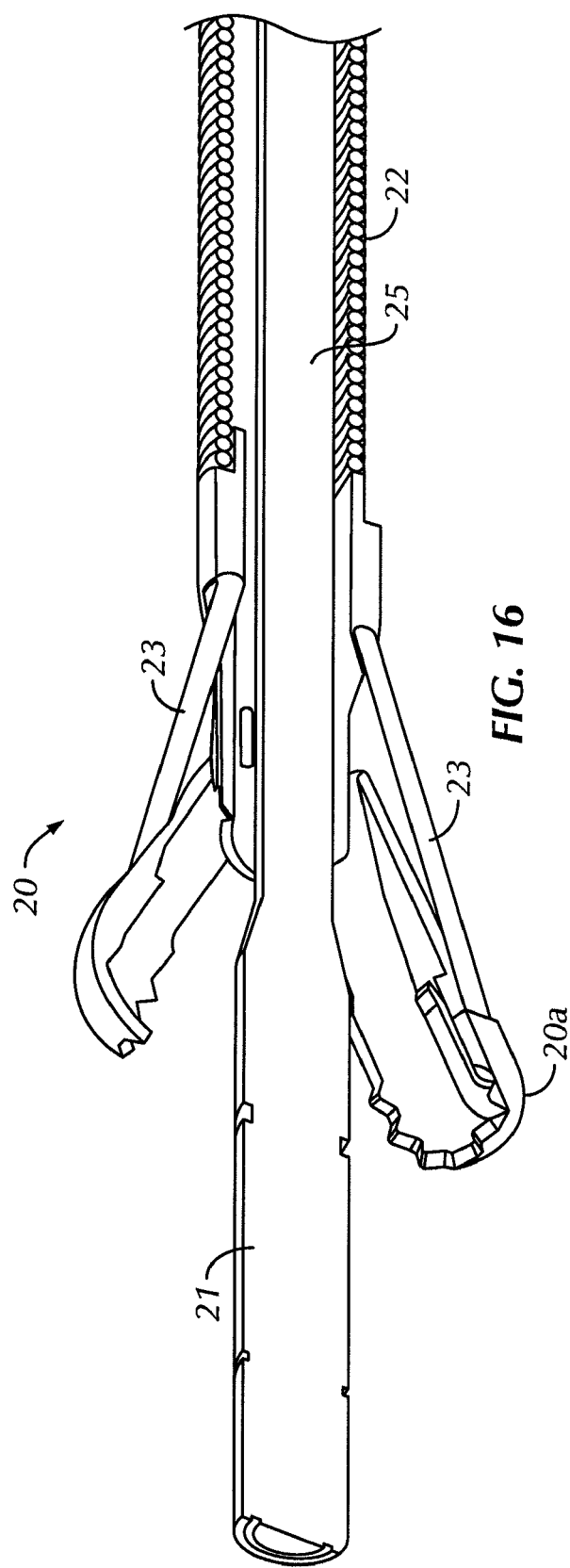
FIG. 16 is a section-view of the forceps assembly of FIG. 15.

Referring now to FIGS. 15 and 16, in a second exemplary embodiment, a forceps assembly 20 may be constructed in a similar fashion to conventional forceps. In this embodiment, the complete mechanism to open and close jaws 20a, sheath 22, and a handle (not shown) are one complete unit comprising forceps assembly 20. Forceps assembly 20, therefore, may form a probe conduit that may accommodate various additional endoscopic tools, which may include, for example, an optical probe 21. As a whole, the forceps assembly 20 may be independent from the endoscopic tool. After use, the forceps assembly 20 may either be discarded entirely or separately disinfected.

As shown in FIG. 15, forceps assembly 20 may comprise jaws 20a, sheath 22, and a conventional handle (as described above). Jaws 20a may be connected to sheath 22 by two beams 23, and to the handle by two wires 24, running through sheath 22 on each side of the body 25 of optical probe 21 (through the probe conduit). Alternatively, the forceps assembly 20, where jaws 20a are located, may comprise a double pivot system, wherein one pivot may be located on each side of jaws 20a.

As shown of FIG. 16, the structure of forceps assembly 20 may be hollow, forming a probe conduit. The probe conduit of forceps assembly 20 may have a large enough interior diameter to shelter endoscopic tools as large as optical probes, for example.

According to this second exemplary embodiment, during the procedure, forceps assembly 20 may first be inserted into an accessory channel of an endoscope. The accessory channel may allow for access to the area to be biopsied. The optical probe 21 may then be inserted into the probe conduit of forceps assembly 20. With jaws 20a open, the endoscopist may scan the area by performing optical biopsies until a suspicious zone that warrants a traditional biopsy for further examination is discovered. Jaws 20a may then be closed, thereby capturing a sample. Both forceps assembly 20 and optical probe 21 may then be retracted from the patient and the sample may be released. Both instruments (forceps assembly 20 and optical probe 21) may then be used for another series of optical and mechanical biopsies for the same patient, as needed. When the procedure is completed, the endoscopist may dispose of the forceps assembly 20 and send the optical probe 21 to the disinfection unit. Alternatively, the forceps assembly 20 may be sent to a disinfection unit for cleaning.

A third exemplary embodiment is shown in FIGS. 17-24. The biopsy unit, in accordance with this third embodiment, is shown in FIG. 17A, and a close-up view of the distal end of the unit is shown in FIG. 17B. Forceps 31, comprising jaws 31a, may be disposed at a distal end of the unit and may form an insertion cartridge 30 (see FIG. 18). Insertion cartridge 30 may be disposed within, and attached to a sleeve 34. Sleeve 34 may be attached to a distal end of a sheath 38. An endoscopic tool, such as an optical probe 32, may be disposed within the interiors of insertion cartridge 30, sleeve 34, and sheath 38. Jaws 31a may be operated by manipulation of a handle 50, employing a main part 51 and a sliding part 52, similar to that discussed above.

Figure 18:
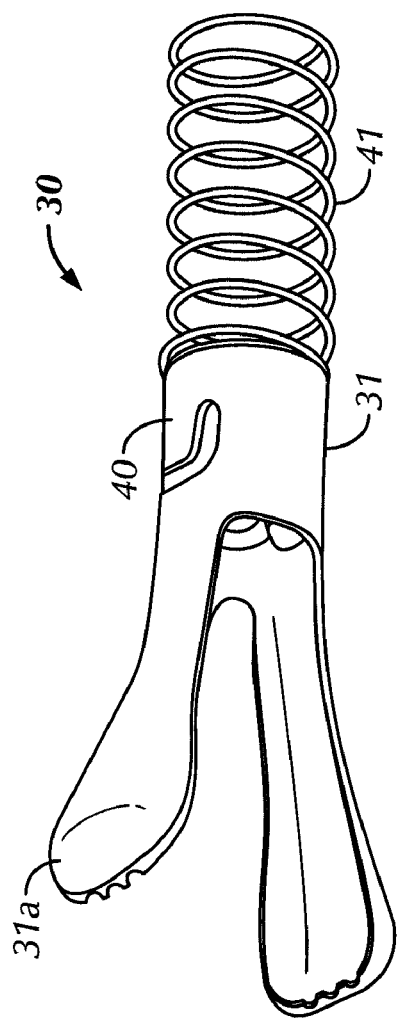
FIG. 18 shows an insertion cartridge in accordance with embodiments of the present disclosure.

FIG. 18 shows the structure of insertion cartridge 30. Insertion cartridge 30 may comprise forceps 31, with jaws 31a, a locking portion 40, and a spring portion 41. As shown, insertion cartridge 30 may be a single, unitary design which may be low cost to construct and may advantageously be readily disposable.

Figure 19:
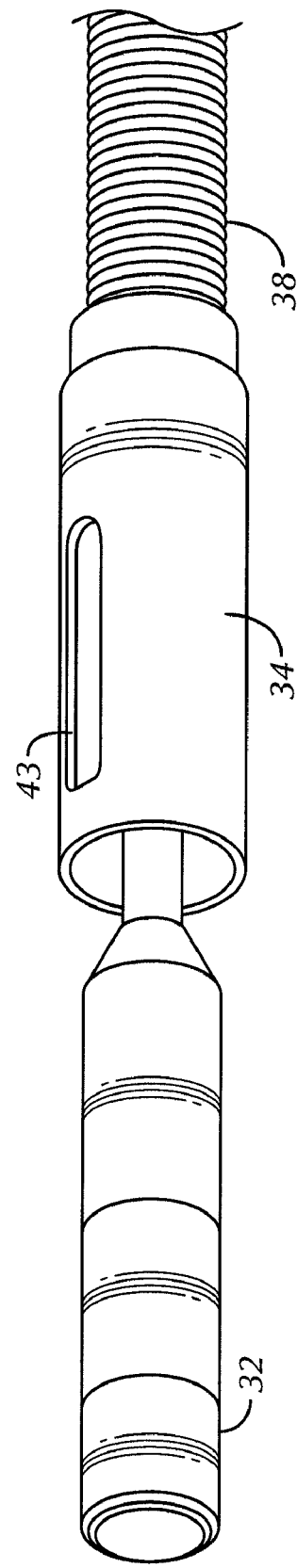
FIG. 19 shows the distal end a biopsy unit in accordance with embodiments of the present disclosure prior to attachment of the insertion cartridge.

FIG. 19 shows the structure of the distal end of the biopsy unit prior to attachment of insertion cartridge 30. As shown in FIG. 19, optical probe 32 may be disposed within sheath 38 and sleeve 34. Further, sleeve 34 may comprise a slot 43 that may receive and lock insertion cartridge 30 into sleeve 34.

Figure 20:
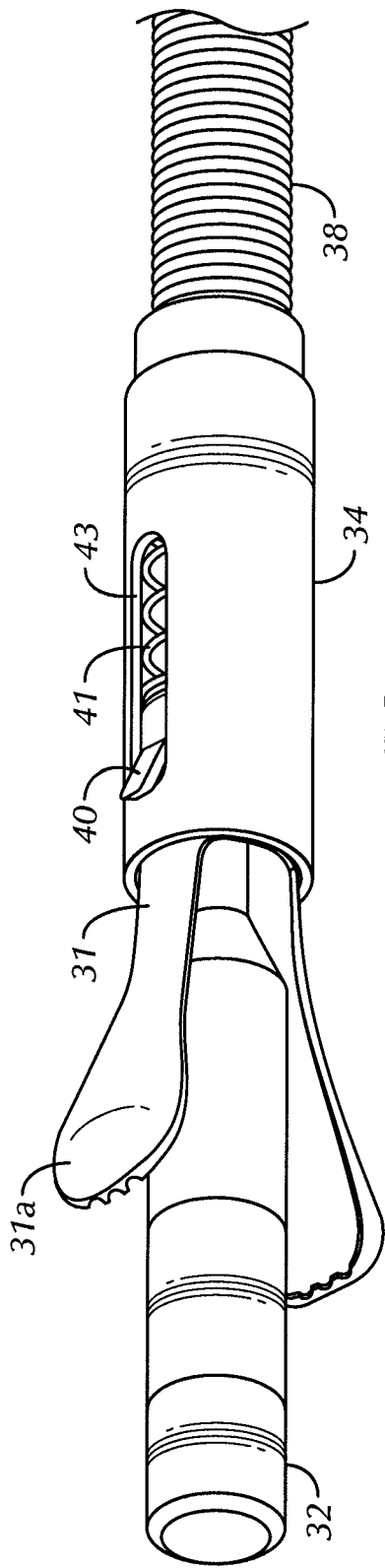
FIG. 20 shows the distal end of the biopsy unit of 17A as assembled.
Figure 21:
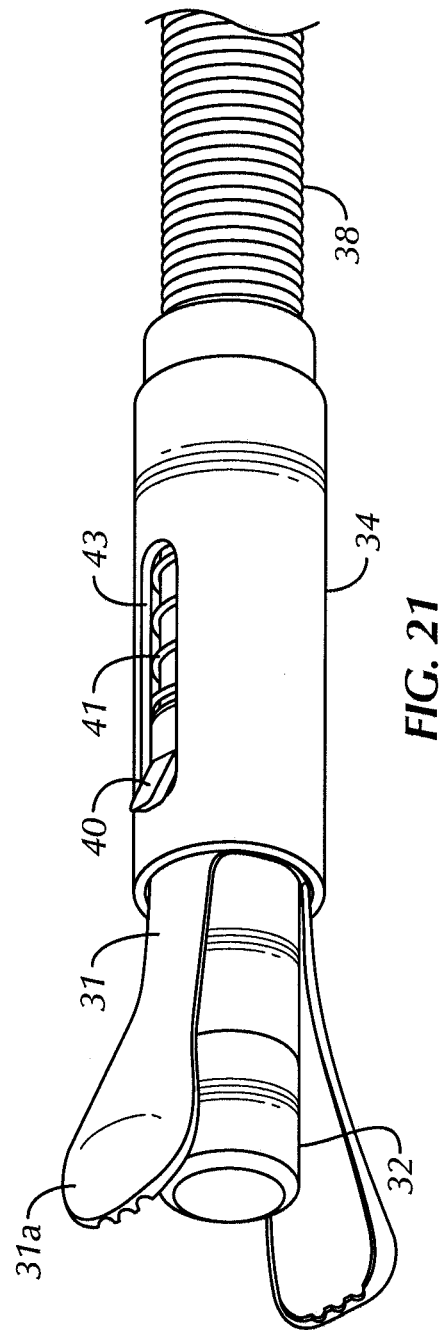
FIG. 21 shows retraction of the optical probe.
Figure 22:
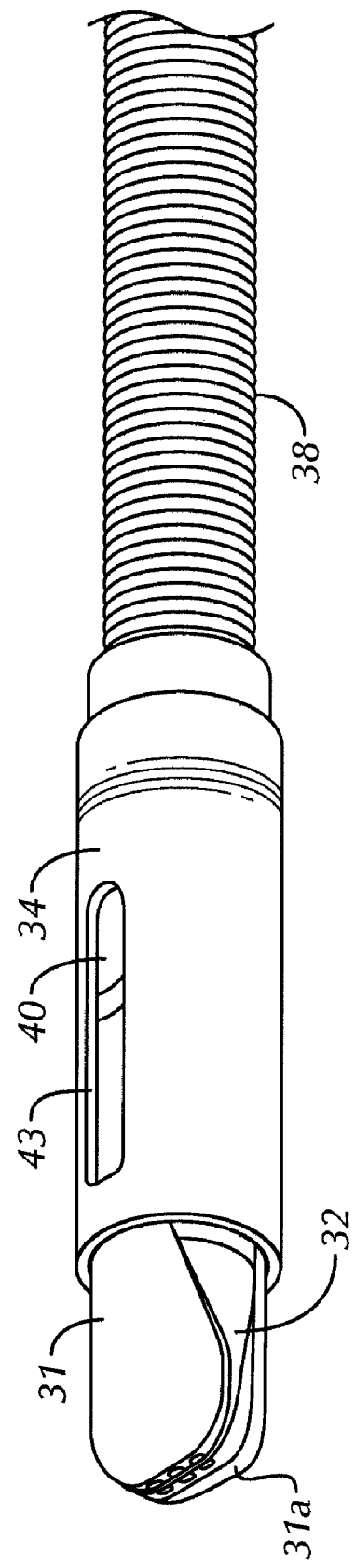
FIG. 22 shows retraction of the optical probe and retraction of the insertion cartridge.
Figure 23:
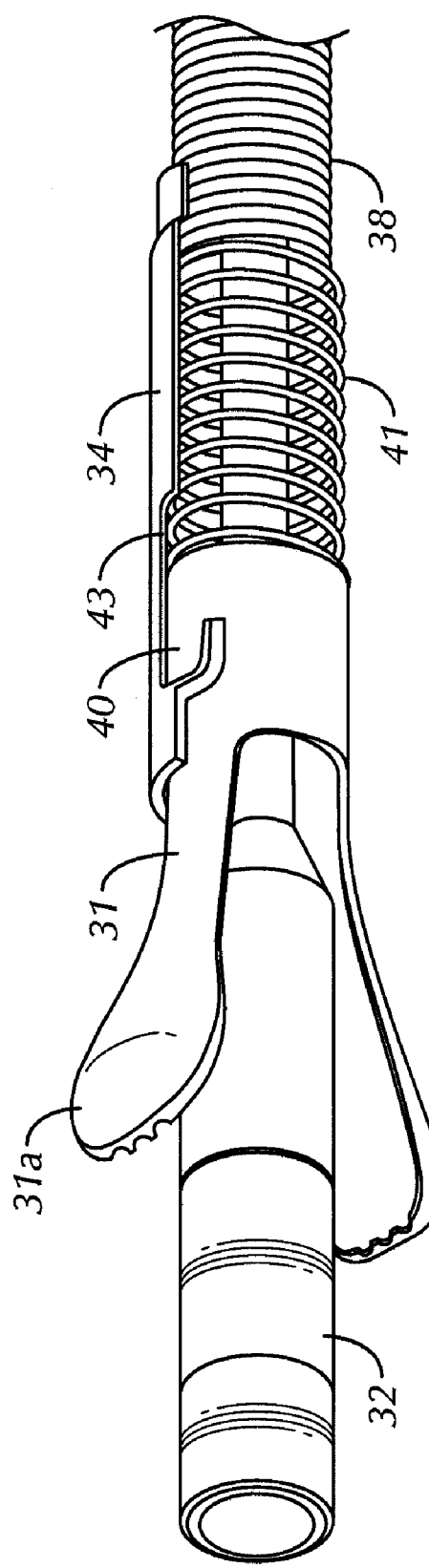
FIG. 23 shows an interior view of the distal end of the biopsy unit of FIG. 17A.

FIGS. 20-22 show the assembled probe and insertion cartridge as it is operated. In FIG. 23, insertion cartridge 30 may attach to sleeve 34 by inserting locking portion 40 into slot 43. Jaws 31a may remain open and optical probe 32 may extend beyond jaws 31a. After a sample is identified for mechanical biopsy, optical probe 32 may be retracted behind jaws 31a, as shown in FIG. 21. Optical probe 32 may then be retracted further, pulling forceps 31 into sleeve 34 and closing jaws 31a, as shown in FIG. 22. As jaws 31a are closing, they may extract and trap the sample behind jaws 31a and the lens of the optical probe 32.

Figure 24:
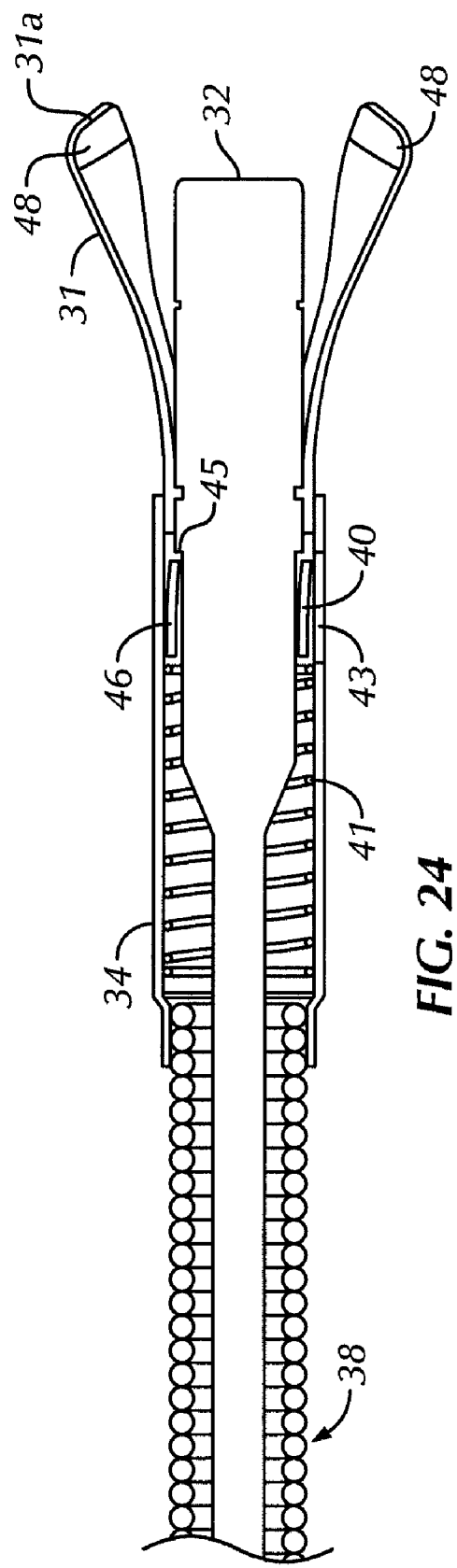
FIG. 24 shows a cross-sectional schematic view of FIG. 23.

Sectional views, shown in FIGS. 23 and 24, detail how forceps 31 operate. Spring portion 41 may be biased so that when insertion cartridge 30 may be inserted into sleeve 34, forceps 31 extend in an open position out of the distal end of sleeve 34. Optical probe 32 may extend beyond jaws 31a, allowing for an optical biopsy.

As noted above, to close jaws 31a, optical probe 32 may be retracted into forceps 31 and sleeve 34, thereby causing contact between stop 45 and tab 46. Stop 45 may be disposed on the proximal end of optical probe 32. Tab 46 may be disposed on the distal end of spring portion 41. When stop 45 contacts tab 46, spring portion 41 may be compressed to cause forceps 31 to retract. When forceps 31 may retract, sleeve 34 may cause jaws 31a to close. In the fully closed position a sample cavity 48 may form, thereby allowing capture, and continued examination, of an extracted sample.

According to this third exemplary embodiment, during the procedure, optical probe 32 may be inserted into sheath 38. Insertion cartridge 30 may then be inserted into sleeve 34, disposed at the distal end of sheath 38. Optical probe 32, insertion cartridge 30, and sheath 38 may then be inserted into an accessory channel of an endoscope. With jaws 31a open, the endoscopist may scan the area by performing optical biopsies until a suspicious zone that warrants a mechanical biopsy for confirmation is discovered. Jaws 31a may then be closed by retracting optical probe 32 into sleeve 34, thereby capturing a sample. Both insertion cartridge 30 and optical probe 32 may then be retracted from the patient and the sample may be released. Both instruments (insertion cartridge 30 and optical probe 32) may be used for another series of optical and mechanical biopsies for the same patient, as needed. When the procedure is completed, the endoscopist may dispose of insertion cartridge 30 and send optical probe 32 and sheath 38 to a disinfection unit. Alternatively, insertion cartridge 32 may be sent to a disinfection unit as well.

Advantageously, when a sample is trapped between the jaws of the forceps and the lens of the optical probe, pursuant to embodiments of the present disclosure, additional examination of the sample may be conducted by the optical probe during extraction of the biopsy unit.

Moreover, by permitting a forceps to be employed, as disclosed, an optical and a mechanical biopsy may be conducted with ease and simplicity, during a single procedure, without extraction and reinsertion of different instruments.

Moreover, forceps, as disclosed herein, may be disposable or re-usable. Allowing for reduced costs of parts and/or cleaning expenses.

Moreover, cross-infection concerns may be avoided through implementation of the biopsy unit disclosed herein. The mechanical complexity of traditional forceps often makes them difficult to clean. Due to this complexity most of the currently available biopsy forceps are single-use items. Optical biopsy probes, in contrast, have a simpler outer structure but are more expensive, and, therefore, are routinely disinfected and re-used several times before they are discarded. Therefore, when an optical device is permanently attached to the forceps, both devices must either be disinfected or thrown away together. In particular, if the relative cost of an optical probe is substantially higher than the forceps, discarding both tools after each use may be wasteful. Alternatively, if both forceps and optical probe are disinfected together, the likelihood of effectively cleaning such a complex assembly may be reduced. However, the combination of a disposable or removable forceps, as disclosed herein, attached to an optical biopsy probe may remove these concerns.

Furthermore, forceps formerly known for use with optical probes may not be mounted on a variety of different optical probes, meaning each different model must be equipped with its own forceps solution. The forceps and biopsy units, disclosed herein, allow for application with many different optical probes, further expanding the variability and usability of the apparatus and procedures disclosed.

In contrast to traditional forceps and endoscopic tools, the presently disclosed biopsy units allow for separate cleaning and/or disposal of the distinct parts, while allowing for both optical and mechanical biopsies during a single procedure.

While the disclosure has been presented with respect to a limited number of embodiments, those skilled in the art, having benefit of this disclosure, will appreciate that other embodiments may be devised which do not depart from the scope of the present disclosure. Accordingly, the scope of the invention should be limited only by the attached claims.

What is claimed is:

1. A method to perform an endoscopic biopsy, the method comprising:
    deploying a mechanical forceps through an accessory channel of an endoscope assembly;
    deploying an optical probe body comprising a distal end on which an optical probe is disposed through the accessory channel of the endoscope assembly to an area of investigation, wherein the mechanical forceps are removable from the optical probe and clip onto the optical probe body immediately before insertion into the accessory channel of the endoscope, wherein the optical probe body comprises a ring configured to engage a proximal end of the mechanical forceps;
    releasably clipping the mechanical forceps onto the optical probe body by engagement of the ring and the proximal end of the mechanical forceps;
    optically evaluating tissue at the area of investigation;
    actuating the mechanical forceps to grasp a sample of the tissue; and
    retrieving the mechanical forceps and the optical probe from the area of investigation through the accessory channel of the endoscope assembly.

2. The method of claim 1, further comprising grasping the sample of the area of investigation after performing an optical biopsy of the area of investigation.

3. The method of claim 1, further comprising re-using the optical probe with a second mechanical forceps at a second area of investigation.

4. The method of claim 3, further comprising disinfecting the optical probe before re-using it at the second area of investigation.

5. The method of claim 1, further comprising deploying the optical probe to the area of investigation through a bore of the mechanical forceps.

6. The method of claim 1, wherein the mechanical forceps comprise a reusable and releasable cartridge.

7. The method of claim 6, further comprising releasably attaching the cartridge to a distal end of a sheath of the mechanical forceps.

8. The method of claim 1, further comprising operating jaws of the mechanical forceps with a handle at a proximal end of the endoscope assembly.

9. The method of claim 1, further comprising operating jaws of the mechanical forceps with at least one pull wire extending through the accessory channel of the endoscope assembly.

10. A biopsy apparatus to investigate tissue through an accessory channel of an endoscope assembly, the biopsy apparatus comprising:
    an optical probe configured to investigate the tissue upon a distal end of an optical probe body extending through the accessory channel; and
    a forceps assembly slidably engaged over the optical probe body, the forceps assembly comprising jaws configured to operate between a closed position and at least one open position, wherein the forceps assembly comprises forceps that are removable from the optical probe and configured to clip onto a ring disposed on the optical probe body immediately before insertion into the accessory channel of the endoscope assembly, wherein the ring engages with a proximal end of the forceps assembly to allow the forceps assembly to releasably clip onto the optical probe body;
    wherein the jaws of the forceps are urged into the closed position as the forceps are retracted within the accessory channel.

11. The biopsy apparatus of claim 10, wherein the jaws comprise a clearance so that the jaws may be closed around the optical probe body.

12. The biopsy apparatus of claim 10, wherein forceps assembly comprises an inner volume when the jaws are in the closed position.

13. The biopsy apparatus of claim 12, wherein the inner volume comprises a probe volume at a proximal end of the forceps assembly and a sample volume at a distal end of the forceps assembly.

14. The biopsy apparatus of claim 13, wherein the forceps assembly is configured to house the optical probe in the probe volume and a tissue sample in the sample volume when the jaws are in the closed position.

15. A method to perform an optical biopsy with the biopsy apparatus of claim 10, comprising:
    deploying the optical probe and the forceps assembly to the area of investigation through the accessory channel, wherein the forceps are positioned behind the optical probe and the jaws are closed about the optical probe body;
    performing an optical biopsy at the area of investigation with the optical probe;
    opening the jaws of the forceps assembly;
    retracting the optical probe within a probe volume of the forceps assembly;
    closing the jaws of the forceps assembly around a tissue sample; and
    retracting the forceps assembly and optical probe through the accessory channel.

16. The method of claim 15, further comprising examining the tissue sample with the optical probe during retraction of the optical probe within the probe volume of the forceps assembly.

17. A biopsy forceps to investigate tissue through an accessory channel of an endoscope assembly, the biopsy forceps comprising:
    a probe conduit extending through the biopsy forceps, wherein the probe conduit is configured to removably receive an optical probe on a distal end of an optical probe body, wherein the biopsy forceps are removable from the optical probe and configured to clip onto the optical probe immediately before insertion into the accessory channel of the endoscope assembly, wherein the optical probe body comprises a ring disposed thereon configured to engage with a proximal end of the biopsy forceps to releasably clip the biopsy forceps to the optical probe body; and a set of jaws configured to operate between a closed position and at least one open position.

18. A method to perform an optical biopsy using the biopsy forceps of claim 17, comprising:

deploying the biopsy forceps to an area of investigation through the accessory channel of the endoscope assembly;

opening the biopsy forceps;

deploying the optical probe on the distal end of the optical probe body to the area of investigation through the probe conduit of the open biopsy forceps;

performing an optical biopsy at the area of investigation with the optical probe;

retracting the optical probe at least partially through the probe conduit;

closing the biopsy forceps around tissue at the area of investigation to be sampled; and retracting the biopsy forceps and the optical probe from the area of investigation through the accessory channel.

* * * * *